US012496084B2

(12) United States Patent
Drake et al.

(10) Patent No.: US 12,496,084 B2
(45) Date of Patent: Dec. 16, 2025

(54) TUNNELING AND INSERTION TOOL FOR IMPLANTABLE MEDICAL DEVICE

(71) Applicant: Medtronic, Inc., Minneapolis, MN (US)

(72) Inventors: Ronald A. Drake, St. Louis Park, MN (US); Lester O. Stener, Hudson, WI (US); Andrea J. Asleson, Maple Grove, MN (US); Mikayle A Holm, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 18/160,271

(22) Filed: Jan. 26, 2023

(65) Prior Publication Data

US 2023/0255654 A1 Aug. 17, 2023

Related U.S. Application Data

(60) Provisional application No. 63/267,888, filed on Feb. 11, 2022.

(51) Int. Cl.
*A61B 17/29* (2006.01)
*A61B 17/32* (2006.01)

(52) U.S. Cl.
CPC .......... *A61B 17/2909* (2013.01); *A61B 17/32* (2013.01); *A61B 2017/2912* (2013.01); *A61B 2017/320056* (2013.01)

(58) Field of Classification Search
CPC ...... A61M 25/0194; A61M 2025/0197; A61N 1/056; A61N 1/0563; A61N 1/0565;
(Continued)

(56) References Cited

U.S. PATENT DOCUMENTS

| | | | |
|---|---|---|---|
| 5,304,119 | A | 4/1994 | Balaban et al. |
| 5,456,699 | A | 10/1995 | Armstrong |

(Continued)

FOREIGN PATENT DOCUMENTS

| | | | |
|---|---|---|---|
| EP | 3263056 A1 | 1/2018 | |
| NZ | 545638 A | 10/2007 | |
| WO | 2021211736 A1 | 10/2021 | |

OTHER PUBLICATIONS

International Search Report and Written Opinion of International Application No. PCT/IB2023/050802 dated Mar. 22, 2023, 11 pp.

*Primary Examiner* — Shaun L David
*Assistant Examiner* — Rachael L Geiger
(74) *Attorney, Agent, or Firm* — Shumaker & Sieffert, P.A.

(57) ABSTRACT

A tool includes a handle, a plunger actuator proximate the handle, a shaft extending from the handle, a plunger, an engagement mechanism. The shaft includes a proximal end and a distal end, and the shaft defines a channel extending along a length of the shaft. A first actuation of the plunger actuator causes the plunger to translate along the length of the shaft in a distal direction. A second actuation of the plunger actuator causes the plunger to translate along the length of the shaft in a proximal direction. The engagement mechanism is disposed on the distal end and is configured to engage an implantable medical device, and release the implantable medical device in response to the plunger exerting a contact force on the implantable medical device exceeding a reaction force of the engagement mechanism when the plunger translates along the length of the shaft in the distal direction.

19 Claims, 5 Drawing Sheets

(58) Field of Classification Search
CPC .... A61N 1/0568; A61N 1/057; A61N 1/0573; A61N 1/0575; A61N 2001/0578; A61N 2001/058; A61N 2001/0582; A61N 2001/0585; A61N 1/0587; A61N 1/059; A61N 1/0592; A61N 1/0595; A61N 1/0597; A61N 1/362; A61B 17/2909; A61B 17/32; A61B 2017/2912; A61B 2017/320056; A61B 17/3468
See application file for complete search history.

(56) References Cited

U.S. PATENT DOCUMENTS

| | | | | |
|---|---|---|---|---|
| 7,018,384 | B2 | 3/2006 | Skakoon | |
| 9,161,775 | B1 | 10/2015 | Katra et al. | |
| 9,399,130 | B2 | 7/2016 | Bonde et al. | |
| 10,258,789 | B2 | 4/2019 | Tischendorf et al. | |
| 10,434,307 | B2 | 10/2019 | Cole | |
| 2004/0054374 | A1* | 3/2004 | Weber | A61B 17/3468 606/107 |
| 2004/0073254 | A1 | 4/2004 | Wyman et al. | |
| 2004/0199140 | A1 | 10/2004 | Rue et al. | |
| 2007/0219564 | A1 | 9/2007 | Rue et al. | |
| 2010/0023042 | A1* | 1/2010 | Dell 'Oca | A61B 17/320016 606/167 |
| 2010/0094252 | A1 | 4/2010 | Wengreen et al. | |
| 2015/0038991 | A1* | 2/2015 | Prior | A61B 17/0482 606/144 |
| 2015/0216533 | A1* | 8/2015 | Gray | A61B 17/12109 606/195 |
| 2016/0038181 | A1* | 2/2016 | Katra | A61B 5/283 606/185 |
| 2017/0049467 | A1 | 2/2017 | Foster et al. | |
| 2017/0136231 | A1* | 5/2017 | Kelly | A61M 25/0147 |
| 2018/0125424 | A1 | 5/2018 | Sick et al. | |
| 2018/0256108 | A1 | 9/2018 | Au-Yeung et al. | |
| 2018/0368875 | A1 | 12/2018 | Castillo et al. | |
| 2019/0117258 | A1 | 4/2019 | Yamauchi et al. | |
| 2019/0125357 | A1* | 5/2019 | Shelton, IV | A61B 17/105 |
| 2020/0113599 | A1* | 4/2020 | Morey | A61B 17/0469 |
| 2020/0353242 | A1* | 11/2020 | Drake | A61N 1/057 |
| 2021/0068840 | A1* | 3/2021 | Allen, IV | A61B 18/1442 |
| 2021/0153813 | A1 | 5/2021 | Bardy et al. | |
| 2021/0353315 | A1* | 11/2021 | Baril | A61B 17/221 |

* cited by examiner

TUNNELING AND INSERTION TOOL FOR IMPLANTABLE MEDICAL DEVICE

This application claims the benefit of U.S. Provisional Application Ser. No. 63/267,888, filed Feb. 11, 2022, the entire content of which is incorporated herein by reference.

TECHNICAL FIELD

The present disclosure relates to medical instruments and, more particularly, to medical instruments for tunneling and inserting implantable medical devices in patients.

BACKGROUND

Implantable medical devices (IMD), such as, for example, cardiac pacemakers, include leads with a lead body containing one or more elongated electrical conductors. The electrical conductors extend through the lead body from a connector assembly provided at a first lead end proximal a housing of an associated IMD to one or more electrodes located at the distal lead end or elsewhere along the length of the lead body. The conductors connect stimulation and/or sensing circuitry within the IMD housing to respective electrodes or sensors. Each electrical conductor is typically electrically isolated from other electrical conductors and is encased within an outer sheath that electrically insulates the lead conductors from body tissue and fluids.

Therapeutic electrical stimulation provided by the leads connected to the IMD may include signals such as pulses or shocks for pacing, cardioversion or defibrillation. In some cases, a medical device may sense intrinsic depolarizations of the heart, and control delivery of stimulation signals to the heart based on the sensed depolarizations. An IMD may also be used to conduct temporary cardiac pacing following the end of an operative procedure, or may be implanted on a temporary basis (for example, for up to about 90 days) to provide pacing support to patients who may have temporary conduction disturbances, or as a bridge between permanent implants in cases of device or system infection. In some examples, conduction disturbances treatable using a temporary IMD may be the result of transcatheter aortic valve replacement (TAVR), or may be caused by alcohol septal ablation, Lyme carditis, and the like.

SUMMARY

In general, this disclosure is directed to tools and techniques for utilizing such tools to tunnel within a patient, such as subcutaneously, e.g., to facilitate implantation of implantable medical devices (IMDs) or components thereof within the space created by tunneling. An example tool may include one or more features that provide advantages, e.g., with respect to ease of delivering and implanting IMDs, during such procedures. For example, the tool may be configurable to act as both a tunneling tool and a delivery tool for delivering the IMD. Further, the tool may include an engagement mechanism disposed at a distal end of a shaft of the tool. The engagement mechanism may be configured to engage an IMD and release the IMD in response to a plunger exerting a contact force on the IMD exceeding a reaction force of the engagement mechanism.

The engagement mechanism may engage an engagement feature of the 1 MB. For instance, the engagement mechanism may include a first protrusion and a second protrusion, and the engagement feature may include a first surface of the IMD defining a first recess configured to receive the first protrusion, and a second surface of the IMD defining a second recess configured to receive the second protrusion. When the first and second protrusions are inserted into the first and second recesses, respectively, the engagement mechanism may resist movement of the IMD, e.g., when advancing the IMD subcutaneously. In this way, the tool may facilitate delivery of the 1 MB when at least a portion of the 1 MB is disposed outside of a channel of the shaft of the tool, which may advantageously improve maneuvering and fixation of the IMD during an implantation procedure.

In some examples, a tool comprises: a handle; a plunger actuator proximate the handle; a shaft extending from the handle, wherein the shaft comprises a proximal end and a distal end, and wherein the shaft defines a channel extending along a length of the shaft; a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to: engage an implantable medical device, and release the implantable medical device in response to the plunger exerting a contact force on the implantable medical device exceeding a reaction force of the engagement mechanism when the plunger translates along the length of the shaft in the distal direction.

In some examples, a system comprises: an implantable medical device comprising an engagement feature; and a tool comprising: a handle; a plunger actuator proximate the handle; a shaft extending from the handle, wherein the shaft comprises a proximal end and a distal end, and wherein the shaft defines a channel extending along a length of the shaft; a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to: engage the engagement feature of the implantable medical device, and release the engagement feature of the implantable medical device in response to the plunger exerting a contact force on the implantable medical device exceeding a reaction force of the engagement mechanism when the plunger translates along the length of the shaft in the distal direction.

In some examples, a method comprises: translating a plunger along a length of a shaft of a tool in a distal direction to form a tunnel in a body of a patient in response to a first actuation of a plunger actuator of the tool; translating the plunger along the length of the shaft in a proximal direction in response to a second actuation of the plunger actuator; engaging an implantable medical device via an engagement mechanism of the tool; and releasing the implantable medical device in response to the plunger exerting a contact force on the implantable medical device exceeding a reaction force of the engagement mechanism when the plunger translates along the length of the shaft in the distal direction.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

The following drawings are illustrative of example embodiments and do not limit the scope of the invention. The drawings are not to scale (unless so stated) and are intended for use in conjunction with the explanations in the following detailed description. Examples will hereinafter be described in conjunction with the appended drawings wherein like numerals denote like elements.

DETAILED DESCRIPTION

Figure 1:
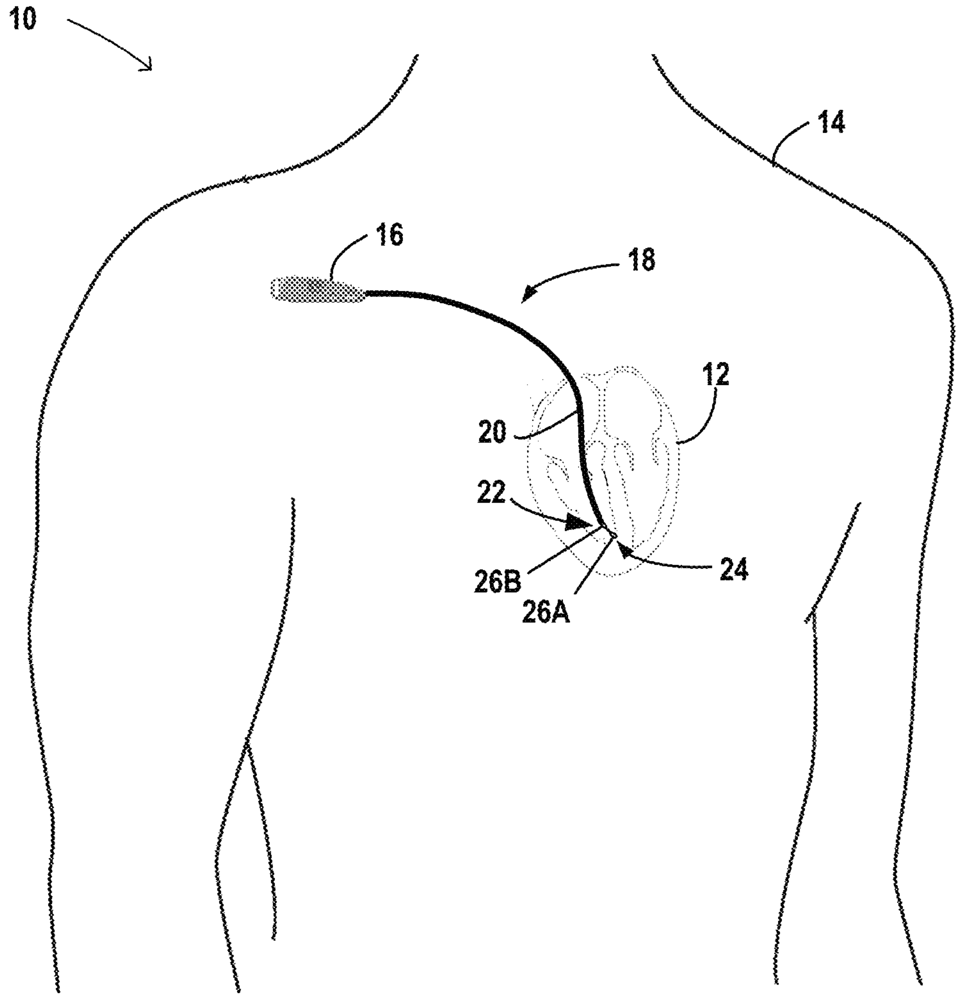
FIG. 1 is a conceptual diagram illustrating an example system that includes an implantable medical device coupled to implantable medical leads.

FIG. 1 is a conceptual diagram illustrating a portion of an example implantable medical device system 10 ("system 10") in accordance with one or more aspects of this disclosure. System 10 may function as a single chamber, e.g., ventricular, pacemaker, as illustrated by the example of FIG. 1, or as dual-chamber pacemaker that delivers pacing to a heart 12 of patient 14.

In the example of FIG. 1, system 10 includes an implantable medical device (IMD) 16. IMD 16 may be configured to couple to an implantable medical lead 18 ("lead 18"). Lead 18 may include an elongated lead body 20 with a distal portion 22. Distal portion 22 of Lead 18 is positioned at a target site 24 within a heart 12 of a patient 14. Distal portion 22 may include one or more electrodes. Target site 24 may be located at a wall of a ventricle of heart 12. Lead 18 may be a bipolar or multipolar lead.

A clinician may maneuver distal portion 22 through the vasculature of patient 14 in order to position distal portion 22 at or near target site 24. For example, the clinician may guide distal portion 22 through the superior vena cava (SVC) to target site 24 on or in a ventricular wall of heart 12, e.g., at the apex of the right ventricle as illustrated in FIG. 1. In some examples, other pathways or techniques may be used to guide distal portions 22 into other target implant sites within the body of patient 14. System 10 may include a delivery catheter and/or outer member (not shown), and lead 18 may be guided and/or maneuvered within a lumen of the delivery catheter in order to approach target site 24.

Lead 18 may include electrodes 26A and 26B (collectively, "electrodes 26") configured to be positioned on, within, or near cardiac tissue at or near target site 24. In some examples, electrodes 26 are configured to function as electrodes in order to, for example, provide pacing to heart 12. Electrodes 26 may be electrically connected to conductors (not shown) extending through lead body 20. In some examples, the conductors are electrically connected to therapy delivery circuitry of IMD 16, with the therapy delivery circuitry configured to provide electrical signals through the conductor to electrodes 26. Electrodes 26 may conduct the electrical signals to the target tissue of heart 12, causing the cardiac muscle, e.g., of the ventricles, to depolarize and, in turn, contract at a regular interval. Electrodes 26 may also be connected to sensing circuitry of IMD 16 via the conductors, and the sensing circuitry may sense activity of heart 12 via electrodes 26. Electrodes 26 may have various shapes such as tines, helices, screws, rings, and so on. Again, although a bipolar configuration of lead 18 including two electrodes 26 is illustrated in FIG. 1, in other examples 1 MB 16 may be coupled to leads including different numbers of electrodes, such as one electrode, three electrodes, or four electrodes.

In one or more examples, 1 MB 16 includes electronic circuitry contained within a polymeric and/or metal enclosure where the circuitry may be configured to deliver cardiac pacing. In the example of FIG. 1, the electronic circuitry within 1 MB 16 may include therapy delivery circuitry electrically coupled to electrodes 26. The electronic circuitry within 1 MB 16 may also include sensing circuitry configured to sense electrical activity of heart 12 via electrodes 26. The therapy delivery circuitry may be configured to administer cardiac pacing via electrodes 26, e.g., by delivering pacing pulses in response to expiration of a timer and/or in response to detection of the activity (or absence thereof) of heart.

Figure 2:
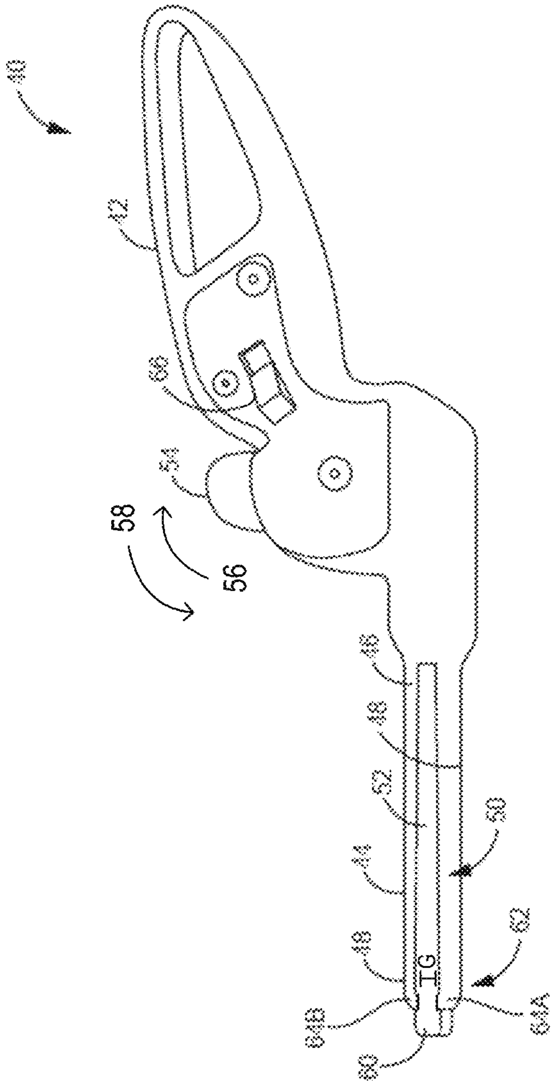
FIG. 2 is a conceptual diagram illustrating an example tunneling and insertion tool.

FIG. 2 is a conceptual diagram of an example tunneling and insertion tool 40 ("tool 40"). System 10 may include tool 40. In accordance with techniques of this disclosure, tool 40 is configured to create a tunnel in which to position 1 MB 16. In other words, tool 40 may be used to tunnel through tissue, e.g., subcutaneous tissue, to create a path and/or space within the tissue. Tool 40 is further configured to insert 1 MB 16 in the space. IMD 16 may be a cardiac device, such as a pacemaker.

As shown in FIG. 2, tool 40 includes a handle 42. A shaft 44 may extend from handle 42. Shaft 44 may include a proximal end 46 and a distal end 48. Shaft 44 may define a channel 50. Channel 50 may extend from proximal end 46 to distal end 48. In some examples, shaft 44 may be about 3.5 inches long. However, other lengths of shaft 44 are contemplated by this disclosure. For example, a length of shaft 44 may be within a range from about 2 to 6 inches.

A plunger 52 may be at least partially disposed within channel 50. Plunger 52 may be an elongate member that is operably coupled to a plunger actuator 54 proximate to handle 42. As discussed in greater detail below, actuation of plunger actuator 54 may cause plunger 52 to translate along the length of shaft 44. In some examples, plunger actuator 54 may be a lever, a dial, a button, a switch, or any other actuator known in the art for controlling translation of plunger 52. In some examples, plunger 52 may be about 4 inches long. However, other lengths of plunger 52 are contemplated by this disclosure. For example, a length of plunger 52 may be within a range from about 2 to 8 inches.

A first actuation of plunger actuator 54, illustratively represented by arrow 56, may cause plunger 52 to translate along the length of shaft 44 in a distal direction. The first actuation of plunger actuator 54 may cause plunger actuator 54 to transition from a first position (shown in FIG. 3A) to a second position (shown in FIG. 3B). A second actuation of plunger actuator 54, illustratively represented by arrow 58, may cause plunger 52 to translate along the length of shaft 44 in a proximal direction. The second actuation of plunger actuator 54 may cause plunger actuator 54 to transition from the second position to the first position.

In some examples, the first actuation may correspond to moving plunger actuator 54 in a substantially proximal direction, and the second actuation may correspond to moving plunger actuator 54 in a substantially distal direction. As discussed in greater detail below, this configuration may advantageously reduce the probability of accidentally releasing IMD 16 when the operator of tool 40 is inserting IMD 16. However, it should be understood that other configurations for actuating plunger actuator 54 are contemplated by this disclosure. Moreover, a suitable configuration for actuating plunger actuator 54 may vary based on the type of plunger actuator 54 (e.g., a lever, a dial, a button, a switch, etc.) of tool 40.

A distal end 60 of plunger 52 is configured to tunnel into tissue to form a passageway for advancement of IMD 16. For instance, responsive to the first actuation of plunger actuator 54, distal end 60 may be disposed beyond distal end 48 of shaft 44 such that distal end 60 contacts a patient's body. As an example, moving plunger actuator 54 in a substantially proximal direction may cause plunger 52 to translate along the length of shaft 44 in a distal direction such that distal end 60 of plunger 52 is disposed beyond distal end 48 of shaft 44. In some examples, distal end 60 may be disposed about 0.25 inches beyond distal end 48. However, distal end 60 may be disposed other lengths beyond distal end 48. For instance, distal end 60 may be disposed about 0.1 inches to 2 inches beyond distal end 48. In some examples, distal end 60 may be generally bulbous and define a blunt tip. In other examples, distal end 60 may be configured to facilitate dissection (e.g., distal end 60 may define a sharp tip).

Tool 40 may include an engagement mechanism 62 configured to engage IMD 16. For instance, shaft 44 may define a first protrusion 64A and a second protrusion 64B (collectively, "protrusions 64") at distal end 48, and engagement mechanism 62 may include protrusions 64. Shaft 44 may define a gap "G" between protrusions 64, and protrusions 64 may engage IMD 16 when IMD 16 is positioned in G (i.e., between protrusions 64). For example, protrusions 64 (as well at least a portion of shaft 44) may be formed from a resilient material (e.g., Acrylonitrile butadiene styrene (ABS), polycarbonate, polyaryletheretherketone (PEEK) thermoplastic polymers, etc.) that is biased to maintain the size of G between protrusions 64. IMD 16 may have one or more dimensions greater than 1 MB 16; however, due to the pliability of protrusions 64, an operator may force IMD 16 between protrusions 64. In some examples, 1 MB 16 may define an engagement feature, discussed in greater detail below, to allow protrusions 64 to "snap" onto 1 MB 16, in this way ensuring a reliable engagement of IMD 16.

Engagement mechanism 62 may be further configured to release IMD 16. For example, engagement mechanism 62 may release 1 MB 16 in response to plunger 52 exerting a contact force on 1 MB 16 exceeding a reaction force of engagement mechanism 62 (e.g., the bias of protrusions 64 to maintain the size of G between protrusions 64) when plunger 52 translates along a length of shaft 44 in a distal direction. Plunger 52 may exert a contact force on IMD 16 when plunger 52 translates along the length of shaft 44 in the distal direction and in turn contacts at least a portion of IMD 16. As such, plunger 52 may exert a contact force on IMD 16 in response to the first actuation of plunger actuator 54.

In some examples, tool 40 includes a lock actuator 66. Lock actuator 66 may be proximate handle 42. Lock actuator 66 may be configured to resist translation of plunger 52 along the length of shaft 44. For example, a first actuation of lock actuator 66 may cause a lock (see FIG. 3A) of tool 40 to engage, thereby resisting translation of plunger 52 along the length of shaft 44 in the proximal direction. A second actuation of lock actuator 66 may cause the lock of tool 40 to disengage, enabling plunger 52 to translate along the length of shaft 44 in the proximal direction.

Figure 3A:
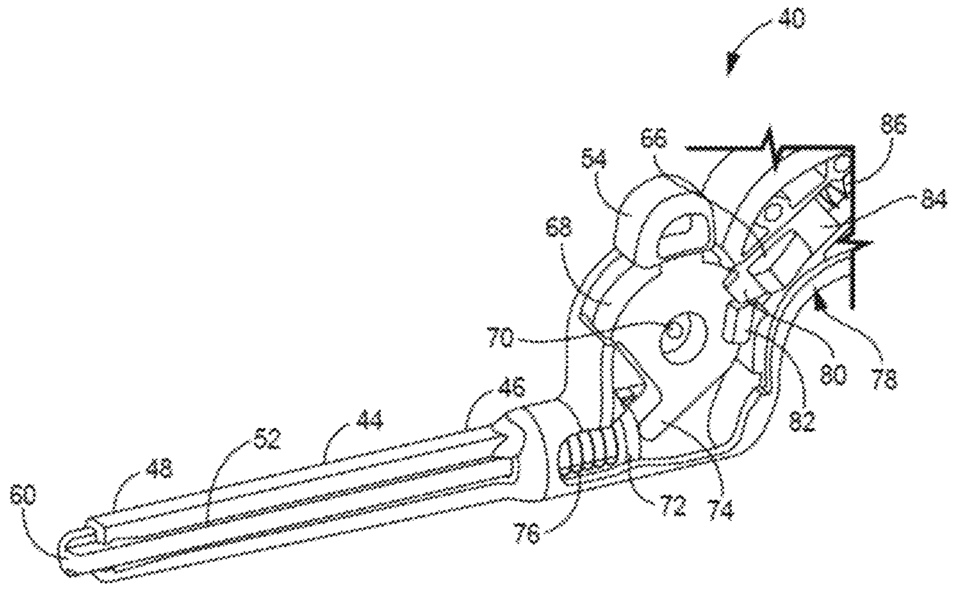
FIG. 3A is a conceptual diagram illustrating an example tunneling and insertion tool with a distal end of a plunger of the tool disposed beyond a distal end of a shaft of the tool.

FIG. 3A is a conceptual diagram of tool 40 with distal end 60 of plunger 52 disposed beyond distal end 48 of shaft 44. As shown in FIG. 3A, a portion of the housing of tool 40 is removed to show inner components of tool 40. As further shown in FIG. 3A, plunger actuator 54 is in a first position.

As noted above, plunger actuator 54 may be operably coupled to plunger 52. For example, plunger actuator 54 may extend from or otherwise be connected to a cam 68. Cam 68 may be a rotating component that rotates about a pivot 70. In some examples, cam 68 may encircle pivot 70. In any case, when an operator actuates plunger actuator 54, cam 58 may correspondingly rotate according to the movement of plunger actuator 54. For instance, when tool 40 is oriented in the manner shown in FIG. 3A, cam 58 may rotate in correspondence with the first actuation of plunger actuator 54 by rotating in a clockwise direction, and cam 58 may rotate in correspondence with the second actuation of plunger actuator 54 by rotating in a counter-clockwise direction.

Cam 58 may be operably coupled to a proximal end 72 of plunger 52. For example, as shown in FIG. 3A, a portion 74 of cam 58 may be in contact with proximal end 72. As such, when cam 58 rotates in a clockwise direction (e.g., in response to the first actuation of plunger actuator 54), portion 74 may exert a force on plunger 52 and cause plunger 52 to translate along the length of shaft 44 in a distal direction. In some examples, plunger 52 may be coupled to a spring 76 (i.e., plunger 52 may be spring-loaded). Spring 76 may be configured to resist translation of plunger 52 along the length of shaft 44 in the distal direction by exerting a proximal force on plunger 52. Accordingly, in these examples, plunger 52 may translate along the length of shaft 44 in the distal direction when portion 74 exerts a force on plunger 52 greater than the force that spring 76 exerts on plunger 52. Furthermore, plunger 52 may translate along the length of shaft 44 in the proximal direction when portion 74 exerts a force on plunger 52 less than the force that spring 76 exerts on plunger 52.

As noted above, a lock 78 may be configured to resist translation of plunger 52 along the length of shaft 44 in the proximal direction. For example, as shown in FIG. 3A, lock actuator 66 may extend from a surface of lock 78. Responsive to the first actuation of lock actuator 66, lock 78 may engage by moving in a substantially distal direction to block rotation of cam 58. When lock 78 is engaged, distal end 80 may protrude distally such that at some point during counter-clockwise rotation of cam 58, a feature 82 (e.g., a protrusion) of cam 68 contacts and is blocked by distal end 80. The contact between distal end 80 and feature 82 may prevent further counter-clockwise rotation of cam 58, which in turn may prevent translation of plunger 52 along the length of shaft 44 in a proximal direction. Conversely, lock 78 may disengage by moving in a substantially proximal direction such that distal end 80 no longer blocks rotation of cam 85.

Figure 3B:
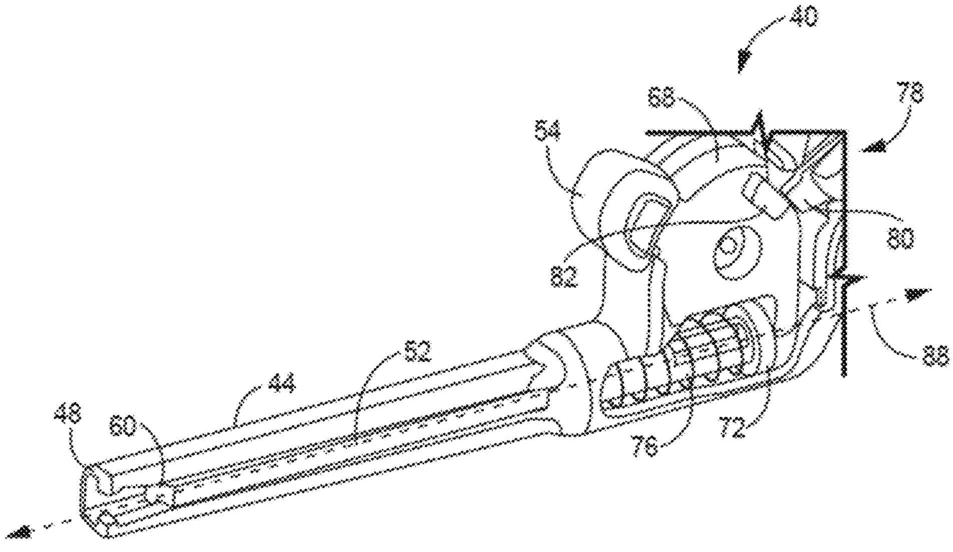
FIG. 3B is a conceptual diagram illustrating an example tunneling and insertion tool with a distal end of a plunger of the tool disposed within the shaft of the tool.

In some examples, lock 78 is spring-loaded. For instance, a proximal end 84 of lock 78 may be coupled to a spring 86. In such examples, second actuation of lock actuator 66 may compress spring 86. As shown in FIG. 3B, feature 82 may block distal end from protruding distally, in this way preventing expansion of (compressed) spring 86 and resulting in lock 78 being spring-loaded. Responsive to the first actuation of plunger actuator 52, feature 82 may no longer block distal end 80 from protruding distally, causing spring 86 to expand and distal end 80 to protrude distally, in effect performing first actuation of lock actuator 66. Automatically performing first actuation of lock actuator in this manner may be advantageous by saving an operator time, which may be particularly valuable in a medical setting.

FIG. 3B is a conceptual diagram of tool 40 with the entirety of plunger 52, including distal end 60 of plunger 52, disposed within shaft 44. As shown in FIG. 3B, a portion of the housing of tool 40 is removed to show inner components of tool 40. As further shown in FIG. 3B, plunger actuator 54 is in a second position.

When plunger actuator 54 is in the first position shown in the example of FIG. 3A, distal end 60 may be disposed beyond distal end 48. When plunger actuator 54 is in the second position shown in the example of FIG. 3B distal end 60 may be disposed within shaft 44. An operator may engage lock 78 when plunger actuator 54 is in the first position, in this way preventing translation of plunger 52 along the length of shaft 44 in the proximal direction. An operator may not be able to engage lock 78 when plunger actuator 52 is in the second position because, as shown in the example of FIG. 3B, feature 82 may prevent distal end 80 from protruding distally. In some examples, when lock 78 is not engaged (and when an operator is not manipulating plunger actuator 54), spring 76 may exert a proximal force on plunger 52 to cause cam 68 to rotate counter-clockwise such that plunger actuator 54 is biased to assume the second position.

In some examples, shaft 44 may not circumscribe plunger 52. For example, a cross-section of shaft 44 transverse to a longitudinal axis 88 of shaft 44 may be concave such that at least a portion of a longitudinal surface of plunger 52 is exposed. This configuration may allow IMD 16 to engage engagement mechanism 62 while at least a portion of IMD 16 is disposed outside of shaft 44, which may advantageously facilitate implantation of IMD 16. For example, at least a portion of IMD 16 being disposed outside of shaft 44 (as opposed to the entirety of IMD 16 being disposed within shaft 44) may increase the reliability of releasing and implanting IMD 16. Moreover, because at least a portion of IMD 16 may be disposed outside of shaft 44, one or more dimensions of IMD 16 (e.g., height, width, etc.) may be greater than the corresponding one or more dimensions of shaft 44.

Figure 4A:
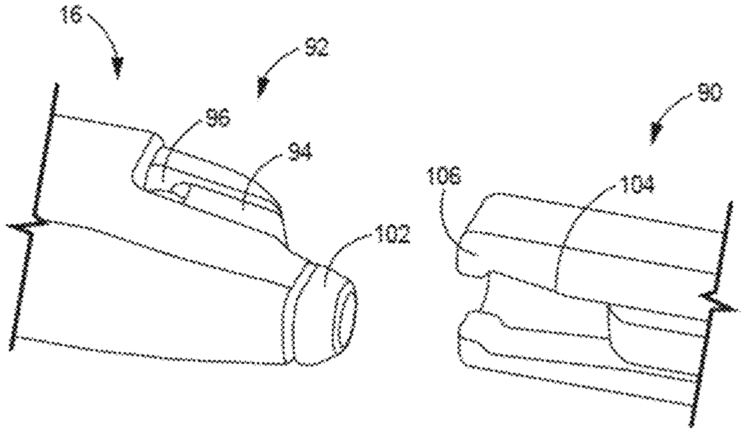
FIGS. 4A-C are conceptual diagrams illustrating an example system including a tunneling and insertion tool and an implantable medical device.
Figure 4B:
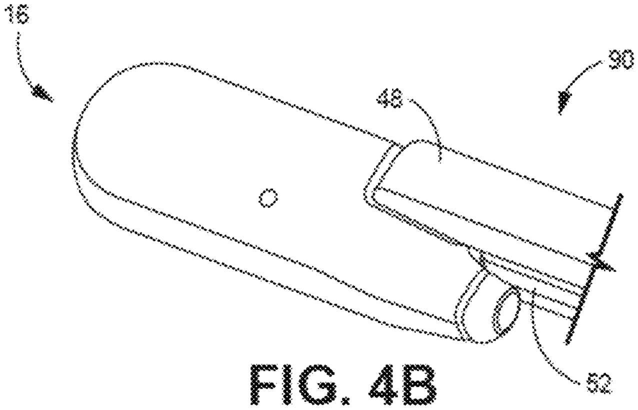
Figure 4C:
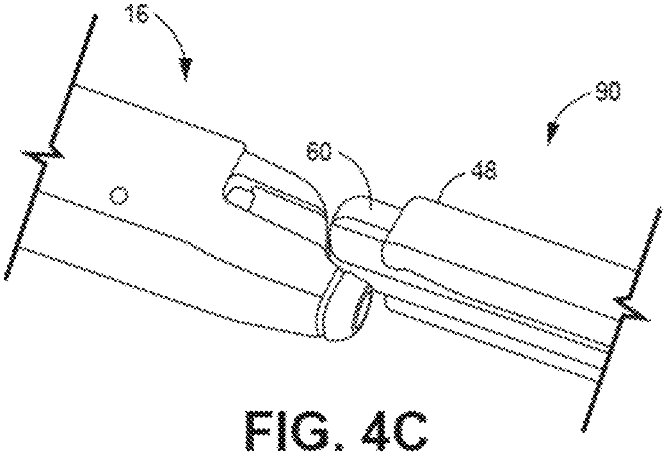

FIGS. 4A-4C are conceptual diagrams of an example system 90 including tool 40 and IMD 16. illustrating operation of engagement mechanism 62. As shown in FIG. 4A, IMD 16 may define or otherwise include an engagement feature 92 configured to engage or otherwise be coupled to engagement mechanism 62.

Engagement feature 92 may include various features that facilitate the engagement of engagement mechanism 62 and engagement feature 92. For example, engagement feature 92 may include a first surface 94 of IMD 16 defining a first recess 96 configured to receive first protrusion 64A. Engagement feature 92 may further include a second surface 98 (not shown) of IMD 16 defining a second recess 100 (not shown) configured to receive second protrusion 64B. In some examples, first surface 94 and second surface 98 may be on opposite sides of IMD 16. In some examples, a width of channel 50 may gradually increase from a first distal point 104 to a second distal point 106 of shaft 44. Second distal point 106 may be distal to first distal point 104. Engagement mechanism 62 may be distal to first distal point 104 and second distal point 106.

First surface 94 may define a first ramp extending from a proximal end 102 of implantable medical device 14 to first recess 96. Similarly, second surface 98 may define a second ramp extending from proximal end 102 to second recess 100. When an operator of tool 40 is inserting IMD 16 between protrusions 64 (e.g., as shown in FIG. 4B), first surface 94 may guide first protrusion 64A toward first recess 96, and second surface 98 may guide second protrusion 64B toward second recess 100. For example, a width of the first ramp may gradually decrease from proximal end 102 to first recess 96, and a width of the second ramp may gradually decrease from proximal end 102 to second recess 100. First recess 96 and second recess 100 may receive first protrusion 64A and second protrusion 64B, respectively.

Engagement mechanism 62 of tool 40 may be configured to release 1 MB 16. For example, as shown in FIG. 4C, engagement mechanism 62 may release 1 MB 16 in response to plunger 52 exerting a contact force on IMD 16 exceeding a reaction force of engagement mechanism 62. Plunger 52 may exert a contact force on IMD 16 by translating along the length of shaft 44 in a distal direction (e.g., in response to the first actuation of plunger actuator 54) until plunger 52 contacts IMD 16.

Figure 5:
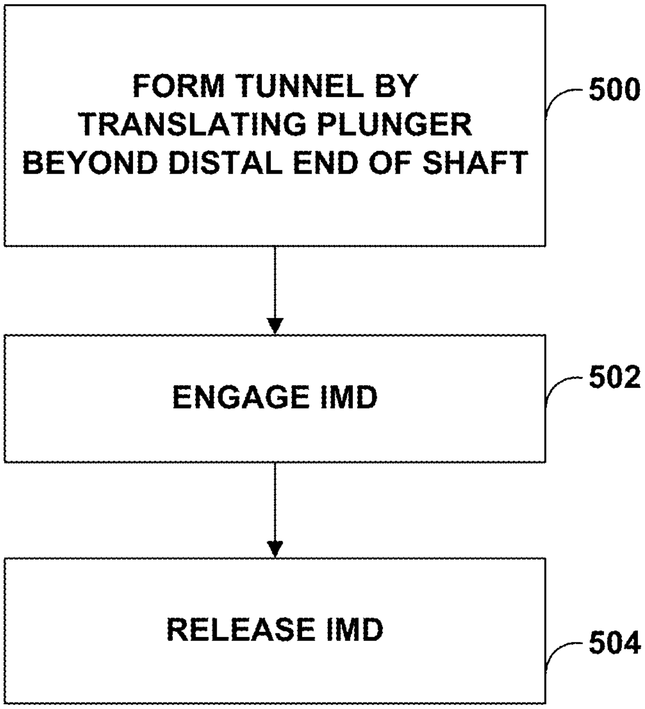
FIG. 5 is a flow diagram illustrating an example technique for operating an example tunneling and insertion tool.

FIG. 5 is a flow diagram illustrating an example technique for operating an example tunneling and insertion tool. According to the example of FIG. 5, tool 40 may form a tunnel for inserting 1 MB 16 (500). Tool 40 may translate plunger 52 along the length of shaft 44 in a distal direction such that distal end 60 is disposed beyond distal end 48. In some examples, tool 40 may translate plunger 52 in response to a first actuation of plunger actuator 54. The first actuation of plunger actuator 54 may be in the direction indicated by arrow 56. That is, an operator may perform a first actuation of plunger actuator 54 by moving plunger actuator 54 in a substantially proximal direction until plunger actuator 54 is in the first position (shown in FIG. 3A).

To prevent plunger 52 from translating along the length of shaft 44 in a proximal direction, tool 40 may engage lock 78. In some examples, tool 40 may engage lock 78 in response to a first actuation of lock actuator 66 when plunger actuator 54 is in the first position such that an operator is not required to apply a proximal force to plunger actuator 54 to maintain the position of plunger 52. The operator may disengage lock 78 by performing a second actuation of lock actuator 66 when desirable (e.g., after forming a tunnel).

An operator may position distal end 60 (which may be disposed beyond distal end 48) proximate an access site on the body of a patient. For example, the operator may position distal end 60 generally orthogonal to a superficial incision of an access site. An operator may apply a distal force to tool 40 to press distal end 60 against and into the access site. In some cases, distal end 48 may be at least partially inserted into the access site.

Tool 40 may engage IMD 16 (502). For instance, engagement feature 92 may engage engagement mechanism 62. In some examples, first recess 96 and second recess 100 may receive first protrusion 64A and second protrusion 64B, respectively. When engagement mechanism 62 and engagement feature 92 are coupled, tool 40 may retain 1 MB 16 in a secure position relative to tool 40 when 1 MB 16 is being advanced into the body of a patient. As such, to advance IMD 16, the operator may apply a distal force to tool 40. To enable engagement feature 92 to engage engagement mechanism 62, distal end 60 of plunger 52 may be disposed within shaft 44. This configuration of tool 40 may correspond to plunger actuator 54 being in the second position (shown in FIG. 3B). Accordingly, in examples where distal end 60 is initially disposed beyond distal end 48 of shaft 44 (e.g., to form a tunnel), an operator may perform the second actuation of plunger actuator 54 such that distal end 60 is disposed within shaft 44, thereby creating space allowing for IMD 16 to be positioned between protrusions 64.

Tool 40 may release 1 MB 16 (504). For example, responsive to an operator using tool 40 to deliver, via the tunnel formed by tool 40, IMD 16 to target site 24 into the tunnel formed by tool 40, plunger 52 may exert a contact force on IMD 16 exceeding a reaction force of engagement mechanism 62 such that engagement mechanism 62 and engagement feature 92 separate (e.g., protrusions 64 are no longer disposed within first recess 96 and second recess 100). In some examples, plunger 52 may exert the contact force in response to the first actuation of plunger actuator 54, which as noted above may correspond to moving plunger actuator 54 in a substantially proximal direction. This configuration may advantageously reduce a probability of accidentally releasing IMD 16 because it may be less likely for an operator to apply a distal force to tool 40 (e.g., while advancing 1 MB 16) and, at the same time, move plunger actuator 54 in a substantially proximal direction (as opposed to a substantially distal direction).

This disclosure includes various examples, such as the following examples.

Example 1: A tool includes a handle; a plunger actuator proximate the handle; a shaft extending from the handle, wherein the shaft includes a proximal end and a distal end, and wherein the shaft defines a channel extending along a length of the shaft; a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to: engage an implantable medical device, and release the implantable medical device in response to the plunger exerting a contact force on the implantable medical device exceeding a reaction force of the engagement mechanism when the plunger translates along the length of the shaft in the distal direction.

Example 2: The tool of example 1, further including a cam that rotates in correspondence with the first actuation of the plunger actuator and the second actuation of the plunger actuator, wherein the cam is operably coupled to the plunger.

Example 3: The tool of example 1 or 2, wherein a distal end of the plunger is configured to be disposed beyond the distal end of the shaft in response to the first actuation of the plunger actuator.

Example 4: The tool of any of examples 1 through 3, wherein the plunger is coupled to a spring, wherein the spring is configured to resist translation of the plunger along the length of shaft in the distal direction.

Example 5: The tool of any of examples 1 through 4, further includes a lock actuator proximate the handle; and a lock, wherein a first actuation of the lock actuator causes the lock to engage, thereby resisting translation of the plunger along the length of the shaft, and wherein a second actuation of the lock actuator causes the lock to disengage.

Example 6: The tool of any of examples 1 through 5, wherein the distal end of the plunger is configured to tunnel into tissue to form a passageway for advancement of the implantable medical device.

Example 7: The tool of any of examples 1 through 6, wherein the shaft defines a first protrusion and a second protrusion at the distal end, and wherein the engagement mechanism defines a gap between the first protrusion and the second protrusion.

Example 8: The tool of any of examples 1 through 7, wherein, from a first distal point on the shaft to a second distal point on the shaft, a width of the channel gradually increases from the first distal point to the second distal point, wherein the second distal point is distal to the first distal point, and wherein the engagement mechanism is distal to the first distal point and the second distal point.

Example 9: The tool of any of examples 1 through 8, wherein a cross-section of the shaft transverse to a longitudinal axis of the shaft along the length of the shaft is concave.

Example 10: The tool of any of examples 1 through 9, wherein the engagement mechanism is formed from a resilient material.

Example 11: A system includes an implantable medical device includes a handle; a plunger actuator proximate the handle; a shaft extending from the handle, wherein the shaft includes a proximal end and a distal end, and wherein the shaft defines a channel extending along a length of the shaft; a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to: engage the engagement feature of the implantable medical device, and release the engagement feature of the implantable medical device in response to the plunger exerting a contact force on the implantable medical device exceeding a reaction force of the engagement mechanism when the plunger translates along the length of the shaft in the distal direction.

Example 12: The system of example 11, wherein the shaft defines a first protrusion and a second protrusion at the distal end, wherein the engagement mechanism defines a gap between the first protrusion and the second protrusion, and wherein the engagement feature includes: a first surface of the implantable medical device defining a first recess configured to receive the first protrusion; and a second surface of the implantable medical device defining a second recess configured to receive the second protrusion.

Example 13: The system of example 12, wherein the first surface defines a first ramp extending from a proximal end of the implantable medical device to the first recess, wherein, from the proximal end to the first recess, a width of the first ramp gradually decreases, wherein the second surface defines a second ramp extending from the proximal end of the implantable medical device to the second recess, and wherein, from the proximal end to the second recess, a width of the second ramp gradually decreases.

Example 14: The system of any of examples 11 through 13, wherein the implantable medical device is configured to be coupled to a lead.

Example 15: The system of example 14, wherein, when coupled to the implantable medical device, the lead extends off-center from a proximal end of the implantable medical device.

Example 16: The system of any of examples 11 through 15, wherein the implantable medical device includes a pacemaker.

Example 17: The system of any of examples 11 through 16, wherein the tool further includes a cam that rotates in correspondence with the first actuation of the plunger actuator and the second actuation of the plunger actuator, wherein the cam is operably coupled to the plunger.

Example 18: The system of any of examples 11 through 17, wherein a distal end of the plunger is configured to be disposed beyond the distal end of the shaft in response to the first actuation of the plunger actuator.

Example 19: The system of any of examples 11 through 18, wherein the plunger is coupled to a spring, wherein the spring is configured to resist translation of the plunger along the length of shaft in the distal direction.

Example 20: The system of any of examples 11 through 19, wherein the tool further includes: a lock actuator proximate the handle; and a lock, wherein a first actuation of the lock actuator causes the lock to engage, thereby resisting translation of the plunger along the length of the shaft, and wherein a second actuation of the lock actuator causes the lock to disengage.

Example 21: The system of any of examples 11 through 20, wherein the distal end of the plunger is configured to tunnel into tissue to form a passageway for advancement of the implantable medical device.

Example 22: The system of any of examples 11 through 21, wherein the shaft defines a first protrusion and a second protrusion at the distal end, and wherein the engagement mechanism defines a gap between the first protrusion and the second protrusion.

Example 23: The system of any of examples 11 through 22, wherein, from a first distal point on the shaft to a second distal point on the shaft, a width of the channel gradually increases from the first distal point to the second distal point, wherein the second distal point is distal to the first distal point, and wherein the engagement mechanism is distal to the first distal point and the second distal point.

Example 24: The system of any of examples 11 through 23, wherein a cross-section of the shaft transverse to a longitudinal axis of the shaft along the length of the shaft is concave.

Example 25: The system of any of examples 11 through 24, wherein the engagement mechanism is formed from a resilient material.

Example 26: A method includes translating a plunger along a length of a shaft of a tool in a distal direction to form a tunnel in a body of a patient in response to a first actuation of a plunger actuator of the tool; translating the plunger along the length of the shaft in a proximal direction in response to a second actuation of the plunger actuator; engaging an implantable medical device via an engagement mechanism of the tool; and releasing the implantable medical device in response to the plunger exerting a contact force on the implantable medical device exceeding a reaction force of the engagement mechanism when the plunger translates along the length of the shaft in the distal direction.

Example 27: The method of example 26, further includes engaging a lock in response to a first actuation of a lock actuator of the tool, wherein engagement of the lock resists translation of the plunger along the length of the shaft; and disengaging the lock in response to a second actuation of the lock actuator.

Various examples have been described. These and other examples are within the scope of the following claims.

What is claimed is:

1. A tool comprising:

a handle;

a plunger actuator proximate the handle;

a shaft extending from the handle, wherein the shaft comprises a proximal end and a distal end, and wherein the shaft defines a channel extending along a length of the shaft;

a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to:

engage an implantable medical device, and release the implantable medical device in response to the plunger exerting a contact force on the implantable medical device exceeding a reaction force of the engagement mechanism when the plunger translates along the length of the shaft in the distal direction, wherein a width of the channel increases from a first distal point on the shaft to a second distal point on the shaft, wherein the second distal point is distal to the first distal point, and wherein the engagement mechanism is distal to the first distal point and the second distal point.

2. The tool of claim 1, further comprising a cam that rotates in correspondence with the first actuation of the plunger actuator and the second actuation of the plunger actuator, wherein the cam is operably coupled to the plunger.

3. The tool of claim 1, wherein a distal end of the plunger is configured to be disposed beyond the distal end of the shaft in response to the first actuation of the plunger actuator.

4. The tool of claim 1, wherein the plunger is coupled to a spring, wherein the spring is configured to resist translation of the plunger along the length of shaft in the distal direction.

5. The tool of claim 1, further comprising:

a lock actuator proximate the handle; and a lock, wherein a first actuation of the lock actuator causes the lock to engage, thereby resisting translation of the plunger along the length of the shaft, and wherein a second actuation of the lock actuator causes the lock to disengage.

6. The tool of claim 1, wherein the distal end of the plunger is configured to tunnel into tissue to form a passageway for advancement of the implantable medical device.

7. The tool of claim 1, wherein the shaft defines a first protrusion and a second protrusion at the distal end, and wherein the engagement mechanism defines a gap between the first protrusion and the second protrusion.

8. The tool of claim 1, wherein a cross-section of the shaft transverse to a longitudinal axis of the shaft along the length of the shaft is concave.

9. The tool of claim 1, wherein the engagement mechanism is formed from a resilient material.

10. A system comprising:

an implantable medical device comprising an engagement feature; and a tool comprising:

a handle;

a plunger actuator proximate the handle;

a shaft extending from the handle, wherein the shaft comprises a proximal end and a distal end, and wherein the shaft defines a channel extending along a length of the shaft, wherein a width of the channel increases from a first distal point on the shaft to a second distal point on the shaft, wherein the second distal point is distal to the first distal point, and wherein the engagement mechanism is distal to the first distal point and the second distal point;

a plunger at least partially disposed within the channel, wherein a first actuation of the plunger actuator causes the plunger to translate along the length of the shaft in a distal direction, and wherein a second actuation of the plunger actuator causes the plunger to translate along the length of the shaft in a proximal direction; and an engagement mechanism disposed on the distal end, wherein the engagement mechanism is configured to: engage the engagement feature of the implantable medical device, and release the engagement feature of the implantable medical device in response to the plunger exerting a contact force on the implantable medical device exceeding a reaction force of the engagement mechanism when the plunger translates along the length of the shaft in the distal direction.

11. The system of claim 10, wherein the shaft defines a first protrusion and a second protrusion at the distal end, wherein the engagement mechanism defines a gap between the first protrusion and the second protrusion, and wherein the engagement feature comprises:

a first surface of the implantable medical device defining a first recess configured to receive the first protrusion; and a second surface of the implantable medical device defining a second recess configured to receive the second protrusion.

12. The system of claim 11, wherein the first surface defines a first ramp extending from a proximal end of the implantable medical device to the first recess, wherein, from the proximal end to the first recess, a width of the first ramp gradually decreases, wherein the second surface defines a second ramp extending from the proximal end of the implantable medical device to the second recess, and wherein, from the proximal end to the second recess, a width of the second ramp gradually decreases.

13. The system of claim 10, wherein the implantable medical device is configured to be coupled to a lead.

14. The system of claim 13, wherein, when coupled to the implantable medical device, the lead extends off-center from a proximal end of the implantable medical device.

15. The system of claim 10, wherein the tool further comprises a cam that rotates in correspondence with the first actuation of the plunger actuator and the second actuation of the plunger actuator, wherein the cam is operably coupled to the plunger.

16. The system of claim 10, wherein a distal end of the plunger is configured to be disposed beyond the distal end of the shaft in response to the first actuation of the plunger actuator.

17. The system of claim 10, wherein the plunger is coupled to a spring, wherein the spring is configured to resist translation of the plunger along the length of shaft in the distal direction.

18. A method comprising:

translating a plunger in a distal direction within a channel extending along a length of a shaft of a tool in a distal direction to form a tunnel in a body of a patient in response to a first actuation of a plunger actuator of the tool, wherein a width of the channel increases from a first distal point on the shaft to a second distal point on the shaft, wherein the second distal point is distal to the first distal point, and wherein the engagement mechanism is distal to the first distal point and the second distal point;

translating the plunger along the length of the shaft in a proximal direction within the channel in response to a second actuation of the plunger actuator;

engaging an implantable medical device via an engagement mechanism of the tool; and releasing the implantable medical device in response to the plunger exerting a contact force on the implantable medical device exceeding a reaction force of the engagement mechanism when the plunger translates along the length of the shaft within the channel in the distal direction.

19. The method of claim 18, further comprising:

engaging a lock in response to a first actuation of a lock actuator of the tool, wherein engagement of the lock resists translation of the plunger along the length of the shaft; and disengaging the lock in response to a second actuation of the lock actuator.

* * * * *